United States Patent [19]

Lehner et al.

[11] Patent Number: 4,594,244
[45] Date of Patent: Jun. 10, 1986

[54] ANTIGENIC MATERIALS

[75] Inventors: Thomas Lehner, Barnet, England; Abu S. M. Giasuddin, Zaria, Nigeria

[73] Assignee: Council of Governors of the United Medical and Dental Schools of Guy's and St. Thomas's Hospitals, London, England

[21] Appl. No.: 579,117

[22] Filed: Feb. 10, 1984

[30] Foreign Application Priority Data

Feb. 14, 1983 [GB] United Kingdom ............... 8303994

[51] Int. Cl.[4] ..................... A61K 39/09; A61K 39/40; C12P 21/00
[52] U.S. Cl. ........................................ 424/87; 424/88; 424/92; 435/68; 435/885; 530/806; 530/825; 530/350
[58] Field of Search ...................... 260/112 R, 112 B; 424/88, 177, 87, 92; 435/68, 885

[56] References Cited

U.S. PATENT DOCUMENTS 4,442,085 4/1984 Colman et al. ................ 424/88 X
4,448,768 5/1984 Colman et al. ................ 424/88 X
4,521,513 6/1985 Russell ........................... 424/87 X

FOREIGN PATENT DOCUMENTS 0009872 4/1980 European Pat. Off. .
0068660 1/1983 European Pat. Off. .
0116472 8/1984 European Pat. Off. ............ 424/92
2060647 5/1981 United Kingdom .

OTHER PUBLICATIONS

J. of Immunology, 135, 1–6 (1985), Lehner et al.
Journal of General Microbiology (1979), 114, 109–151, Russell.
Infection and Immunity, vol. 29, No. 3, 1980, pp. 999–1006, Russell et al.
Infection and Immunity, vol. 28, No. 2, 1980, 489–493, Russell et al.
Biological Abstracts 73, Abstract 39207, 1982.

Primary Examiner—Howard E. Schain
Attorney, Agent, or Firm—Oblon, Fisher, Spivak, McClelland & Maier

[57] ABSTRACT

An antigenic material having a molecular weight of 3800–4500, and useful in the preparation of an anticaries vaccine is produced from a known antigenic material, antigen I/II of molecular weight 185,000 daltons obtained from the culture supernatant of *Streptococcus mutans*. The smaller molecular weight fraction of the invention contains the same antigenic determinants as the known 185,000 dalton material but the lower molecular weight material can be used with less side effects. The antigenic material can be used for the production of vaccine preparations that could be administered parenterally or by topical application to the gums.

14 Claims, No Drawings

ANTIGENIC MATERIALS

DESCRIPTION

This invention relates to antigenic materials suitable for use in vaccines against dental caries.

The antigenic components of *Streptococcus mutans* have been extensively studied since it was recognised that this was the major organism responsible for the development of dental caries. It has previously been recognised that immunisation with whole cell or cell-wall preparations of *S. mutans* may produce undesirable side effects and hence there has been a desire to produce vaccines containing one or more pure specific antigens to confer the necessary protection against dental caries.

Four predominantly protein antigens (designated I to IV) have previously been identified in the culture supernatant of *S. mutans* by immunodiffusion and immunoelectrophoresis against corresponding rabbit antisera (see Archs Oral Biol. 23 7–15, Russell and Lehner). Antigen I referred to in that paper, which is now known as antigen I/II, has a molecular weight, as determined by sodium dodecyl sulphate-polyacrylamide gel electrophoresis (SDS-PAGE) in the range of 175,000 to 195,000 daltons. Glycoproteins with similar molecular weights to antigen I/II have been isolated by other workers, as has a glycoprotein with a molecular weight of 29,000 daltons (see J. Gen. Micro. 114 109–115, R. R. B. Russell). Further investigations on the antigen I/II molecule (MW 185000 daltons) has shown that antigen I (MW 150,000 daltons) and II (MW 48,000 daltons) are associated in this single molecule (see UK Patent Publication No. 2060647A and Infection and Immunity 28 486–493, M. W. Russell et al). This latter reference also indicates that antigen II can be separated and isolated by pronase digestion of antigen I/II followed by column chromatography, while it is disclosed that antigen I can be isolated from antigen I/II by affinity chromatography (see Infection and Immunity 29 999–1006, M. W. Russell et al).

There has now been found, in accordance with the present invention, an antigenic substance derivable from *S. mutans* having a molecular weight as determined by SDS-PAGE in the range of 3,800–4,500 daltons. Surprisingly, despite the low molecular weight of this material, it is found to contain both the antigenic determinants I and II which are present in the material of 185,000 daltons.

The low molecular weight antigen, which will hereinafter be referred to as antigen X, has certain characteristics as listed below. The molecular weight in conjunction with some or all of the other characteristics may be used in identifying the material of the present invention:

1. It has a molecular weight as determined by SDS-PAGE in the range of 3,800–4,500 daltons,
2. It is immunogenic in experimental animals, forming precipitating antibodies,
3. It reacts with antisera raised against antigen I, antigen I/II or antigen II as well as with antisera raised against itself, but does not react with antisera raised against antigen III,
4. It is distinct from serotype polysaccharide antigens, glycerol teichoic acid, dextran and similar glucans, and does not synthesise glucans from sucrose,
5. It is substantially of a proteinaceous nature,
6. It absorbs ultra-violet light strongly between 220 and 250 nm (maximum at 230 nm),
7. Its immunogenic activity is destroyed by the enzyme pronase.

The present invention relates not only to the above antigen X but also antigenic substances which are of equivalent immunological activity to antigen X. In the Example which follows, an amino acid analysis is given for the 3,800 dalton peptide prepared as described in the Example. It will be appreciated, however, that the invention is not restricted to a material having precisely this composition, nor precisely the amino acid sequence of the natural product, where modifications in the amino acid composition and sequence do not alter the immunogenic activity as discussed below.

Antigen X is isolable from *S. mutans* though it need not necessarily be obtained from this source, or indeed from a Streptococcus organism. As illustrated in the Example which follows, antigen X can be obtained from a starting material comprising the 185,000 dalton antigen termed antigen I/II. Antigen II of 48000 daltons can be separated and isolated by pronase digestion of antigen I/II followed by column chromatography, while antigen I of 150000 daltons can be isolated by affinity chromatography. Antigen X of the present invention, while being of much smaller size, than either antigen I or antigen II, still retains both antigenic determinants I and II. Without wishing to be bound by any theory, it is suggested that the 185,000 dalton material may contain repeating units of I/II antigenic determinants of which the smallest unit corresponds to antigen X of the present invention. If that is the case, it is possible either that *S. Mutans* synthesises antigens with these two determinants in a range of molecular sizes, or that the 185,000 dalton material is broken down by the streptococcal proteases inside the cells or in the extra cellular fluid.

When antigen X is to be isolated from the organism, it can be prepared using a starting material of antigen I/II prepared by any previously known method. A particular method is indicated in the following Example and reference is also made to the method in British Patent publication 2060647A. In broad terms, antigen X can be obtained from antigen I/II either by subjecting it in an excess quantity to polyacrylamide gel electrophoresis using a urea containing gel, isolating from the gel a fraction having a molecular weight in the range of 3800–4500 daltons. Overloading of the 185,000 dalton preparation e.g. at least a ten-fold excess of the normal quantity, on 15% SDS-PAGE in the presence of 6M-urea revealed the presence of the antigen of the present invention which was not evident when normal quantities (20 μg protein/cm slot) were used. A convenient overload figure is 280±30 μg protein/cm slot. Alternatively, antigen I/II can be heated and the heated material subjected to gel filtration when antigen X can be isolated.

Although the technique using SDS-PAGE as described in the Example part d (i) enables a satisfactory preparation of antigen X, it has also been found possible to produce a single band of 3,800 dalton material by boiling the starting antigen I/II in 4% SDS buffer for seven minutes to dissociate and release the components and then sieving it through Sephacryl S-200 with the same buffer (see part d (ii) in the Example which follows). The fact that antigen X can be recovered after denaturing antigen I/II from which it is prepared suggests that the three dimensional antigenic structure must have been restored in the final product to that resembling the starting material. However, as is illustrated in the Example, pronase digested both the antigenic determinants of the 3,800 peptide within thirty minutes, which differs from the result with the 185,000 dalton material in which antigen I' was readily digested but antigen II remained intact even after 16 hours of digestion. This suggests that both antigenic determinants I and II may be exposed to enzyme action in antigen X whereas in the larger molecule antigen II may be concealed.

Antigen X has been found to have two amino-terminal residues, glycine and alanine, which suggests either that the preparation is an equimolar mixture of two peptides with very similar molecular weights or that the peptide is made up to two chains linked by a disulphide bridge. However, as the molecular weight of the peptide is unchanged after treatment with mercaptoethanol, it is more likely that the low molecular weight peptide is a mixture of two separate chains, though the invention is not to be bound by this theory.

The carbohydrate content of antigen X has been analysed in terms of the total monosaccharide concentration and the results are given in part e (iii) of the Example. The findings suggest that the carbohydrate content of antigen X is negligible, as a 2% level would allow for carbohydrate corresponding to a molecular weight of only 80 daltons, and the two samples tested gave percentages of 1.64 and 2.08. Antigen X also differs from antigen I/II in failing to show lipid content ad determined by thin layer chromatography. It therefore seems that antigen X is a protein with no lipids and only a trace of carbohydrate which need not be present especially if the antigen is obtained from sources other than *S. mutans.*

The present invention provides antigen X either in substantially pure form or associated with other materials. It may, for example, be mixed with other antigens of different immunogenicity but is preferably completely free from cells and cell-wall fragments. Most preferably, it is in substantially pure form such that on SDS-PAGE it exhibits a single protein band. If necessary, affinity chromatography may be used to achieve the desired purity of the product.

Antigen X from sources other than *S. mutans* may have an amino acid sequence corresponding exactly to the product from that source or, alternatively, may be formed by altering amino acids within the sequence where these changes do not affect the immunogenic activity. The alteration can take the form of an omission or addition of one or more amino acids and/or a modification of one or more amino acids. Such changes are permitted provided the product has unaltered immunogenic activity. While such changes in the antigen would, perhaps, be detectable by monoclonal antibodies raised against the natural product, this is not considered to be an indication that their immunogenic activity is altered. Equivalent immunogenic activity is shown by the fact that antibodies produced by the modified antigen X will neutralise the same bacterium as the natural product and by the ability of the modified antigen X to combine in vitro with antibodies produced by the natural product.

Particular immunogenic equivalents may be formed by modifying reactive groups within the natural sequence or, particularly, the N-terminal amino groups and/or the C-terminal carboxyl groups. Other equivalents include salts formed with acids and bases, particularly physiologically acceptable inorganic and organic acids and bases. Esters and amides may also be formed with the carboxyl group. Such modifications of the antigen are preferably carried out where they enable the production of a more stable active peptide which is less susceptible to enzymic breakdown in vivo.

It is preferred to place the antigen in as similar a conformation or conformational environment as possible to that which it occupies in vivo. The precise structure of the antigen is not known, though, as indicated above, it is believed to comprise two separate but similar peptide chains. It may therefore be appropriate to introduce crosslinking into the material in order to stabilise it and this may possibly be achieved by suitable replacement of amino acids by ones which are capable of covalently bonding with others in the other chain; in particular, cysteine may be introduced to form a disulphide bond with another chain. Alternatively, it may be appropriate to loop the peptide by linking together ends of chains, e.g. with an amide link between chain termini.

Antigen X of the present invention is useful for providing protection against dental caries. This in vivo production of antibodies specific to the antigenic determinants I and II on antigen X is believed to be an important aspect of their action. It is for this reason that the present invention also extends to antigenic substances of equivalent immunological activity.

Vaccines containing antigen X or immunogenic equivalents may be prepared by conventional methods and administered by various routes. They will usually be in a form suitable for injection or for oral administration. Thus, the antigen may for example be formulated in a diluent or on a solid carrier. The injectible solutions will usually be given subcutaneously or intramuscularly. Oral methods of administration may produce a effect systemically or locally in the mouth, and orally active preparations can be formulated as a gel, toothpaste, mouthwash or chewing gum.

Although the vaccines will usually be given to produce protection against attack of dental caries, it is also envisaged that the vaccine may be given to a patient already having caries. As previously indicated, antigen X may also be mixed with other antigens of different immunogenicity; this may be necessary to ensure that antibodies reacting with all serotypes of *S. mutans* are produced by the vaccines.

The antibodies to antigen X and its immunogenic equivalents also form part of the present invention. Thus, while the antigen of the present invention may be given to a patient to induce the production of antibodies, the antibodies themselves may be given directly for use in passive immunisation where this seems appropriate. Such antibodies may be prepared by the general method for preparing antisera given in section (b) of the Example which follows. Alternatively, monoclonal antibodies can be prepared by the genera technique of Kohler and Milstein in which, for example, a mouse host is injected with antigen X of the present invention, spleen cells from the immunised host mouse isolated and hybridised with myleoma cells and appropriate hybridomas isolated that will produce monoclonal antibodies that will subsequently protect a host against dental caries. Antibodies, including monoclonal antibodies, can be formulated for passive immunisation as indicated above for the formulation of antigen X including the solid or liquid formulations such as gels, toothpastes, mouthwashes or chewing gums.

Dosage levels are selected in order to give high levels of protection and will generally be lower than those envisaged for antigen I/II. As illustrated in section (f) of the Example which follows, antigen X is capable of producing a significant response with only 10 μg of protein and using Allugel as adjuvant. One reason why smaller amounts of material may be effective is that antigen X apparently increases the production of only the helper T-cells and not the suppressor T-cells. A suitable dosage for human immunisation by the subcutaneous route may conveniently be of the order of 0.01 to 0.5 mg given with aluminium hydroxide or another suitable adjuvant. A frequency of administering the vaccine to young patients will conveniently be: 6 months, 2 years, 5 years and 10 years, with the initial dose being accompanied by adjuvant and the subsequent doses being administered without adjuvant and being about ½ to ¼ the level of antigen in the initial dose. The frequency of administration can, however, be determined by monitoring the antibody levels in the patient.

The present invention accordingly also provides a pharmaceutical composition comprising antigen X, an immunogenic equivalent thereof or an antibody to either of these, in combination with a physiologically acceptable diluent or carrier. In addition, it provides a method of treating a mammalian, particularly a human, patient, in order to provide at least some protection against dental caries by administering to the patient a composition as defined above.

The antigen of the present invention may also be used in assaying antibodies to antigenic determinants I and II, e.g. where these are being monitored to determine the level and timing of vaccination needed. For this purpose, the antigen will normally be attached to an inert carrier such as a dextran, e.g. Sepharose. Alternatively, the antigen may be used in affinity chromatography in order to isolate such antibodies.

Like antigen I/II, antigen X of the present invention is capable of eliciting the production of antibodies to antigens I and II giving a high level and breadth of protection against dental caries. Antibodies to antigen X can be completely absorbed by the antigen I/II and are indistinguishable from those induced by antigen I/II itself. It has the added advantages, however, that in being smaller, it is better defined and hence less likely to give rise to side effects, and also it activates T-helper cells but not T-suppressor cells.

The following Examples illustrate the invention. Example 1 describes a typical method for preparing antigen X from naturally occurring materials and gives details of its properties and activity.

EXAMPLE 1

Preparation of Antigen X

(a) Culture of S. mutans

Streptococcus mutans serotype c (Guy's strain) was grown in 12 liters of pre-warmed Todd-Hewitt broth (Oxoid) at 37° C., using an overnight culture in 100 ml of Todd-Hewitt broth as an inoculum. The growth was continued for 60–65 hours. The culture supernatant was separated by centrifugation in a continuous flow rotor at 37,000 g. (Guy's strain of S. mutans serotype C is a typical strain of serotype C of S. mutans and many similar strains of serotype C of S. mutans are available from Culture Collections including the ATCC in USA, e.g. ATCC 27607

(b) Extraction and purification of Antigen I/II

The protein antigens in the resulting culture supernatant were precipitated with 75% ammonium sulphate. The precipitate was spun down, dissolved in urea-tris buffer, dialysed against water and chromatographed on a diethylaminoethyl (DEAE)—cellulose column (Whatman DE52,30×1.5 cm). The column was eluted with 6M urea—0.01M tris buffer (ph 8.0) containing 0.05M sodium chloride and the fractions were tested in single radial immunodiffusion (SRID) against antiserum to antigen I/II (prepared as described below). The positive fractions were pooled, dialysed against water, lyophilised and then dissolved in 1% ammonium bicarbonate and gel filtered on a Sepharose 6B column (Pharmacia, Great Britain, Ltd, 90×2.5 cm); with the same buffer. The eluate was monitored at 280 nm and 3 ml fractions were tested by SRID against antiserum to I/II. The fractions containing antigen I/II were pooled and lyophilised.

Antisera for use in SRID described above were raised in New Zealand white rabbits by intramuscular injections of 1 mg of antigen I/II in Freund's complete adjuvant, followed three weeks later by subcutaneous injection of 1 mg antigen I/II in Freund's incomplete adjuvant. Blood was taken three or more weeks after the last immunisation. Single radial immunodiffusion was used for the identification of antigens in the fractions in 1.0% agarose gel containing 1–2% antiserum in veronal buffer (pH 8). (Other antisera used in this Example were also prepared by this method.)

(c) Detection of Antigens by SDS-PAGE

High molecular weight antigens were detected by SDS-PAGE on 7.5% polyacrylamide gels in a vertical slab gel apparatus as described previously (see UK Patent publication 2,060,647A). Low molecular weight antigens were detected by 15% SDS-PAGE in the presence of 6M-urea (Bethesda Research Laboratories (BRL), USA, Biologue 1981). The 15% resolving gel contained 0.1M-sodium phosphate buffer (pH 7.2), 0.1% SDS, 0.02% sodium azide and 6M-urea, and a 7.5% polyacrylamide stacking gel in the same buffer was used. The gel was prepared to provide sample wells as described in UK Patent publication 2060647A and was overloaded with the antigen I/II preparation prepared in step (b) above (280±30 μg protein/cm slot). Gels were run overnight at 70 V and stained with Coomassie Brilliant Blue.

A pre-stained protein molecular weight standard mixture (BRL, USA), containing ovalbumin (43000), α-chymotrypsinogen (25700), β-lactoglobulin (18400), lysozyme (14300), cytochrome c (12300), bovine trypsin inhibitor (6200) and insulin A and B chains (3000), were used to determine the molecular weights of the antigens. A number of components were detected having a lower molecular weight than antigen I/II itself; in 27 out of 29 preparations of the starting antigen I/II a low molecular weight peptide having a molecular weight which varied from 3800 to 4500 daltons was detected.

(d) Purification of low molecular weight antigens

(i) SDS-PAGE

A sample of 2.5 mg per gel of the starting antigen I/II prepared as under (b) above was loaded, after equilibration with the sample buffer, on 15% polyacrylamide—6M urea gels and electrophoresed as described in section (c) above, using 3 different quantities of antigen I/II. After electrophoresis, the gel was sliced into five sections according to the molecular weight ranges (1)>43000, (2)<43,000>25,700, (3)<25,700>18,400, (4)<18,400>6,200 and (5)<6,200. The slices were minced separately by forcing each through a hypodermic syringe and the antigens were then extracted three times with 0.01M tris-HCl buffer (pH 8.0), containing 0.05% SDS and 1 mM phenyl methylene sulphonyl fluoride (PMSF) at 37° C. for 36-48 hours. The three extracts from each slice were pooled, passed through a glass fibre filter under vacuum, dialysed extensively against water at 4° C. and lyophilised. The dialysis tubing used had a molecular weight cut-off of 1000 daltons. The lyophilised material was reconstituted in 0.85% NaCl, spun for 3 minutes at 25,000 g and the supernatant was collected.

The proteins and peptides eluted from each of the 5 gel slices were assayed for their protein content by the method of Lowry et al (see J. Biol. Chem 193 265-275, (1951)) with bovine serum albumin as standard. They were also assayed for their antigenicity with antisera to antigen I/II, I, II and III by SRID, the antisera all being produced as previously indicated for antisera to antigen I/II. The results are given in the following Table 1 for the three different loadings of antigen I/II.

ml fractions were collected. The absorbance of each fraction was also measured at 230 nm at which wavelength they absorbed more strongly than at any other wavelength in the u.v. spectrum. Fractions recorded at 230 nm were pooled over the following molecular weight ranges: (1) >33,000 (2) 33,000-21,500, (3) 21,500-13,700, (4) 13,700-8,000, (5) 8,000-3,000, (6) 3,000-2,300 and (7) <2,300. At absorbance of 230 nm, fraction 1,5 and 6 showed individual peaks, fraction 2 showed a shoulder on the major peak of fraction 1 and fraction 3 was taken as the descending part of the latter. Fraction 4 showed absorbance.

The pooled fractions were dialysed at room temperature in tubing with a molecular weight cut-off of 1,000, in three steps as follows: (i) against water for 12-24 hours with 2-3 changes; (ii) against 40% methanol for 48 hours, with a change at 24 hours and (iii) against water again for 48 hours, with several changes of water. They were then lyophilised and reconstituted in 1.0 ml of 0.85% NaCl. The reconstituted materials were spun for 3 minutes at 25,000 g and the supernatants were collected. The protein content and antigenicity were assayed for each of these 7 fractions as indicated under section d(i) and the results are given in following Table 2.

TABLE 1

| Quantity of antigen I/II loaded (mg) | Fraction No. | Molecular Weight | Protein Content μg | % Yield | Antibodies to antigens I | II | III |
|---|---|---|---|---|---|---|---|
| 5.0 | 1 | >43000 | 1330 | 26.60 | + | + | + |
|  | 2 | <43000 > 25700 | 190 | 3.80 | + | + | + |
|  | 3 | <25700 > 18400 | 178 | 3.05 | + | + | Trace |
|  | 4 | <18400 > 6200 | 126 | 2.52 | + | + | − |
|  | 5 | <6200 | 198 | 3.96 | + | + | − |
| 5.7 | 1 | >43000 | 1230 | 24.60 | + | + | + |
|  | 2 | <43000 > 25700 | 180 | 3.60 | + | + | + |
|  | 3 | <25700 > 18400 | 165 | 3.30 | + | + | Trace |
|  | 4 | <18400 > 6200 | 110 | 2.20 | + | + | − |
|  | 5 | <6200 | 180 | 3.60 | + | + | − |
| 6.5 | 1 | >43000 | 1211 | 24.22 | + | + | + |
|  | 2 | <43000 > 25700 | 152 | 3.04 | + | + | + |
|  | 3 | <25700 > 18400 | 158 | 3.16 | + | + | Trace |
|  | 4 | <18400 > 6200 | 106 | 2.12 | + | + | − |
|  | 5 | <6200 | 157 | 3.14 | + | + | − |

+ presence of the antigenic determinant
− absence of the antigenic determinant

As can be seen from the above Table 1, as the amount of antigen loaded was increased, so the percentage yield of various fractions decreased. Antigenic determinant I/II was present in all fractions in each case, including the lowest molecular weight fraction (fraction 5) which comprised predominantly antigen X of M.W. 3800-4500. A variable amount of antigenic determinant III was also detected in fractions 1, 2 and 3 but not in 4 or 5.

(ii) Sephacryl S-200 Column Chromatography

Gel filtration of antigen I/II was carried out on a Sephacryl S-200 column (88 cm×1.6 cm) and equilibrated with 0.1M-tris-HCl (pH 8.0), containing 4.0% SDS and 0.02% sodium azide. The column was calibrated using α-chymotrypsinogen (25,700), soyabean trypsin inhibitor (21,500), ribonuclease A (13,700), insulin (6,000), insulin A chain (2,300) and glutamyl-glycyl-phenylalanine (352) as standards. A 10 mg sample of the antigen I/II prepared as under (b) above was dissolved in 1.5 ml of the elution buffer, boiled for 10 minutes and cooled before it was loaded on to the column. The effluent was monitored continuously at 254 nm and 1.5

TABLE 2

| Fraction No. | Molecular Weight | Protein Content μg | % Yield | Single radial diffusion with antisera to SA I/II | I | II | III |
|---|---|---|---|---|---|---|---|
| 1 | >33000 | 2031 | 20.31 | + | + | + | − |
| 2 | <33000 > 21500 | 650 | 6.50 | + | + | + | + |
| 3 | <21500 > 13700 | 210 | 2.10 | + | + | + | Trace |
| 4 | <13700 > 8000 | 152 | 1.52 | + | + | + | − |
| 5 | <8000 > 3000 | 138 | 1.38 | + | + | + | − |
| 6 | <3000 > 2300 | 64 | 0.64 | + | + | + | − |
| 7 | <2300 | 60 | 0.60 | + | + | + | − |

The fractions were then tested for efficiency of separation on both 15% polyacrylamide—6M urea and 7.5% polyacrylamide gels as described under (c) above. Fraction 5 (mol. wt.<8000>3000) showed a single band corresponding to a molecular weight of about 3800 as calculated from the gel. Fractions 6 and 7 also showed bands equivalent to a molecular weight less than 4000 but the protein concentrations were less than that in fraction 5 (see Table 2).

As indicated in Table 2, the SRID tests showed that antigen I and II were present in all seven fractions and that antigen III was absent in all but 2, with a trace in fraction 3. The presence of antigens I and II but not III in fractions 5, 6 and 7 was confirmed by the solid phase radio-immunoassay (see Clin. Exp. Immunol. 43 417–428). Of 6 Sephacryl column separations carried out, all yielded the antigen of 3800 daltons in fraction 5 but this material was detected in only 4/6 of the fractions 6 and 7.

It has also been found that if 0.1% SDS is used instead of 4% SDS in the elution buffer, all but fractions 1 and 7 contain the 3800 dalton antigen I/II, with increasing intensity of staining from fraction 2 to 6. However, with the 0.1% SDS the higher molecular weight proteins were not separated completely. In contrast, with 4% SDS the low molecular weight peptide was found only in fraction 5 and to a lesser extent in 6 and 7. This provides evidence, though the invention is not to be bound by this theory, that the 3,800 dalton antigen is tightly bound to antigen I/II (185,000 daltons), along with other proteins of intermediate molecular weights which are demonstrable on the 15% polyacrylamide—6M urea gel.

(e) Analysis of Antigen X (i) Amino acid analysis

The protein samples were hydrolysed at 110° C. with 5.7M HCl containing 0.1% phenol (w/v), in sealed evacuated tubes, after flushing several times with $N_2$ for 24 hours and analysed on a Rank Hilger Chromaspek J 180 instrument. N-terminal residues were determined by dansylation of the protein samples by the procedure of Gray (Methods Enzymol 25 121–138 (1972)) and identification of dansyl-amino acids by thin layer chromatography on polyamide layer sheets (see Biochem. Biophys. Acta 133 369–370 (1967)). Dansyl chloride and polyamide layer sheets were obtained from BDH Chemicals, Poole, Dorset, UK.

The amino acid composition of the 3,800 dalton peptide is given in following Table 3 and compared with that for the 185,000 dalton antigen I/II.

TABLE 3

|  | 3,800 dalton peptide | | 185,000 dalton protein | |
| --- | --- | --- | --- | --- |
|  | mol amino acid/ mol peptide | mol amino acid/ 1000 mol | mol amino acid/ mol protein | mol amino acid/ 1000 mol |
| Asp | 3.1 | 78 | 172.6 | 99 |
| Thr | 3.0 | 76 | 165.4 | 95 |
| Ser | 3.5 | 87 | 136.5 | 79 |
| Glu | 2.2 | 55 | 182.9 | 105 |
| Pro | 1.4 | 35 | 106.6 | 61 |
| Gly | 7.3 | 182 | 119.5 | 69 |
| Ala | 6.1 | 152 | 204.9 | 118 |
| Cys | 0 | 0 | 0 | 0 |
| Val | 2.2 | 55 | 105.6 | 61 |
| Met | 0 | 0 | 0 | 0 |
| Ile | 2.0 | 51 | 82.3 | 47 |
| Leu | 3.4 | 85 | 105.3 | 61 |
| Tyr | 1.6 | 39 | 91.4 | 53 |
| Phe | 0.6 | 14 | 58.3 | 34 |
| His | 0.7 | 18 | 61.0 | 35 |
| Lys | 1.2 | 31 | 146.3 | 84 |
| Arg | 1.7 | 42 | n.d. | n.d. | n.d. not determined

From the above Table 3 it can be seen that the 3,800 dalton peptide has a relatively lower content of charged amino acids but a relatively higher content of non-polar residues than the 185,000 material. As no precautions were taken to convert cysteine and methionine residues to stable derivatives prior to hyrolysis, no significance can be ascribed to the absence of these two amino acids in each preparation. Dansylation of the 3,800 mol. weight fragment revealed two amino acids, alanine and glycine, as amino terminal residues, together with trace amounts of a large number of other amino acids. 38 or 40 amino acid residues were shown to make up the antigen.

(ii) Proteolytic digestion of the antigen

42 μg of the 3,800 d.antigen was taken up in 600 μl of 0.1 M-tris/HCl and incubated at 37° C. with pronase (ennzyme:protein, 1:100 (w/w)). Samples of 100 μl were taken at 0 min, 15 min, 30 min, 2 hours, 4 hours and 6 hours and boiled for 10 minutes. Samples were analysed for antigen I and II determinants by the solid-phase radio-immunoassay technique (see Clin. Exp. Immunol 43 417–428). Both the antigenic determinants I and II were partially digested by 15 minutes' treatment and completely digested by 30 minutes' treatment, as can be seen from Table 4 below which shows the effect of pronase treatment expressed as a percentage binding of $_{125}I$ in the radioimmunoassay.

TABLE 4

| Antiserum to: | Duration of pronase treatment (min) | | | |
| --- | --- | --- | --- | --- |
|  | 0 | 15 | 30 | 60 |
| Antigenic determinant I/II | 1.46 | 0.63 | 0.22 | 0.23 |
| Antigenic determinant I | 1.40 | 0.75 | 0.28 | 0.38 |
| Antigenic determinant II | 1.29 | 0.59 | 0.22 | 0.20 |
| Normal rabbit serum | 0.05 | 0.02 | 0.05 | 0.03 |

(iii) Carbohydrate analysis

The total monosaccharide contents of the 3,800 dalton material and the 185,000 dalton material were determined by the method of Clamp (see Biochem. Soc. Symp. 40 3–16 (1974)) on a Pye 204 gas chromatograph. The column (1.5 m×4 mm) was packed with 10% SE-30 (w.v.) on Chromosorb W HP AWDMCS, mesh size 100–120. D(—)arabinose was used as standard. Two samples of the 3,800 dalton material were found to contain 1.64% and 2.08% (w/w) of monosaccharide in contrast to a mean (±SD) of 6.57 (±1.63)% of 10 samples of the 185,000 dalton material.

(iv) Lipid analysis

Total lipid was extracted with chloroform and methanol (2:1, v/v) by the method of Folch et al (see J. Biol Chem. 266 497–509 (1957)) and analysed by thin layer chromatography on plates coated with silica gel H containing ammonium sulphate as described by Kaulen (see Anal. Biochem 45 664–7 (1972)). Plates were developed with hexane, diethyl ether and acetic acid (60:30:1, v/v) until the solvent front reached the top of the plate. After thorough drying the lipids were detected by exposure to iodine vapour for 3–5 minutes.

Thin layer chromatography revealed the presence of free fatty acids, triglycerides and cholesterol esters, with $R_f$ values slightly different from the mammalian lipid standards, in the 185,000 dalton antigen. As the lipid extract from 40 μg of the 3,800 dalton material gave only a spot at the origin which was also present in the control, antigen X was considered to be free of lipids.

(f) Immunological properties of Antigen X (i) In monkeys

A vaccine is prepared by dissolving the 3,800 dalton antigen (Example 1d(ii) fraction 5) in 0.85% w/v saline containing an equal volume of Alhydrogel (Miles Laboratories Ltd) (aluminium hydroxide suspension) to give a vaccine containing 10 μg antigen per ml. 1 ml doses of this vaccine were injected subcutaneously in about 2 kg rhesus monkeys. Within 14 days a very significant increase in the IgG class of antibody was detected by radioimmunoassay, comparable with that elicited by the 185,000 dalton antigen. This was associated with a very marked increase in helper but not suppressor function with the 3,800 daltong antigen, but both helper and suppressor functions were elicited by the 185,000 daltons antigen, as indicated by the results in Table 5 which follows. (The helper and suppressor functions were generated by culture in Marbrook flasks for 24 hours and then determining the number of Jerne antibody forming cells, after cooperative culture for 4 days (see Infect. Immun. 26 903, J. Immunol 124 2384 and Nature 292 770)).

TABLE 5

| Day | Helper Function (AFC)* | | Suppressor Function (%) | | Serum Antibodies (% binding) serum at 1:100 | |
|---|---|---|---|---|---|---|
| | 3800 | 185,000 | 3800 | 185,000 | 3800 | 185,000 |
| 0 | 5 | 0 | 12 | 0 | 0.6 | 0.6 |
| 7 | 242 | 208 | 11 | 94 | 0.4 | 1.9 |
| 14 | 177 | ND | 30 | 100 | 10.5 | 17.2 |
| 28 | 190 | 200 | 13 | 100 | 9.8 | 11.7 |
| 85 | 177 | 190 | 0 | 95 | 7.9 | 7.4 |

*AFC = antibody forming cells.

(ii) In man

The helper and suppressor functions of the 3,800 and 185,000 daltons preparations were compared using human lymphocytes in vitro. This revealed (see results in Table 6 below) that whilst the 185,000 dalton antigen induced both help (with 1000 ng) and suppression (with all other doses), the 3800 dalton antigen induced help only with doses of 1-10,000 ng antigen as was observed in rhesus monkeys.

TABLE 6

| Function | 3800 dalton Strep. Antigen | | | | | | 185,000 dalton Strep. Antigen | | | | | |
|---|---|---|---|---|---|---|---|---|---|---|---|---|
| Dosage | 0 | 1 | 10 | 100 | 1000 | 10,000 | 0 | 1 | 10 | 100 | 1000 | 10,000 |
| % Help* | 0 | 100 | 100 | 77 | 96 | 100 | 0 | 2 | 13 | 0 | 100 | 0 |
| % Suppression* | 2 | 12 | 2 | 12 | 9 | 28 | 12 | 88 | 100 | 96 | 2 | 100 |

*% Help or Suppression calculated from the antibody forming cells (AFC) given by mouse spleen helper cells: 277 ± 9 AFC and Strep. antigen alone 53 ± 12 AFC.

(iii) Side reactions

Neither local nor systemic side reaction was observed. The blood indices remained normal and there was no change in the haemoglobin or in the red or white blood cell count. Antibodies to heart homogenate were assayed by the solid phase radioimmunoassay and were not detected.

EXAMPLE 2

1. Subcutaneous vaccination

A vaccine is prepared as described in Example 1, f(i). 1 ml doses were injected subcutaneously in divided doses in the arm and thigh of 4 young rhesus monkeys. Five control monkeys were injected with saline only. All monkeys were then kept on a human type of diet, containing about 15% sugar (Lehner, T., Challacombe S. J. and Caldwell J. 1975, Archs, oral Biol. 20, 299). Two of the monkeys were reinjected 2 weeks later with 10 μg of a similar vaccine but without the aluminium hydroxide adjuvant. The monkeys were examined regularly for dental caries, serum antibodies and for colonisation with Strep. mutans.

The results of this examination is given in Table 7 and show significant reduction in carious lesions in the immunised monkeys, mean ± standard error ($0.25 \pm 0.25$) as compared with the control animals ($2.4 \pm 0.75$) after a period of about 1½ years. Analysis by the Student's test showed these results to be significant at the 5% level ($t = 2.453$, d.f.7, $p < 0.05$).

There was a significant increase in the serum IgG antibody titre assayed by a radioimmunoassay (cpm) in the immunised ($2788 \pm 884$), as compared with the control monkeys ($472 \pm 123$). However, the difference in the number of colony forming units failed to reach a significant level.

2. Topical gingival vaccination

A topical vaccine was prepared by dissolving 3800 dalton antigen X in 0.85% w/v saline at a concentration of 500 μg per ml of saline solution and to increase its permeability through the gingival crevicular epithelium 50% dimethyl sulphoxide (DMSO) was added to the solution. About 200 μg of this vaccine was applied topically to the gingival sulci of the upper and lower jaws of 2 young rhesus monkeys and kept in place for about 5 minutes by means of a preformed silicone rubber appliance which fitted exactly the teeth and gums. The appliance was made by taking an impression of the upper and lower jaw with Optosil (Bayer Dental), constructing a tray with cold cure acrylic, taking further impressions with the same material and then lining it with Xantopren plus material (Bayer Dental). On inserting the appliance, fine digital pressure was applied 30 times in rapid succession, in order to facilitate the vaccine to reach the crevicular epithelium. This procedure was repeated 4 times over a period of a month, repeated twice at 3 months and once at 5 months.

Two control monkeys were injected subcutaneously with saline. All monkeys were placed on the human type of diet. The monkeys were examined for dental caries, serum and gingival fluid, IgG antibodies, salivary IgA antibodies and colonisation of Strep. mutans.

The results of 2 immunised and 2 control monkeys (see Table 8) suggest that gingival immunisation prevents dental caries by the presence of gingival fluid IgG class of antibodies and salivary IgA class of antibodies. These are associated with a marked decrease in the number of colonies of Strep. mutans. An important feature is the absence of a significant increase in serum antibodies to Strep. mutans. Hence, gingival immunisation with antigen X induces protection against dental caries, in the absence of serum antibodies and therefore any systemic side effects. There were no detectable local changes in the gingiva.

TABLE 7

| Rhesus Monkey | Dose of SA injected | No. of carious lesions | Serum IgG Antibody titre (cpm) |
|---|---|---|---|
| 1 | 10 μg × 2 | 1 | 5204 |
| 2 | 10 μg × 2 | 0 | 2979 |
| 3 | 10 μg × 1 | 0 | 1725 |
| 4 | 10 μg × 1 | 0 | 1246 |
|   |   | *0.25 (±0.25) | *2788 (±884) |
| 5 | 0 | 2 | 290 |
| 6 | 0 | 4 | 131 |
| 7 | 0 | 0 | 759 |
| 8 | 0 | 4 | 440 |
| 9 | 0 | 2 | 740 |
|   |   | *2.4 (±0.75) | *472 (±123) |

*Mean (±standard error)

TABLE 8

| Rhesus monkey | No. of gingival immunissations | No. of carious lesions | Colony forming units of Strep. mutans | Gingival fluid Serum IgG* | IgG* | Salivary IgA* |
|---|---|---|---|---|---|---|
| 1 | ×7 | 0 | 10.5 | 0 | 42 | 44.2 |
| 2 | ×7 | 0 | 15.8 | 0 | 50.6 | 36.4 |
| 3 | 0 | 7 | 59.8 | 0 | 0 | 0 |
| 4 | 0 | 2 | 72.5 | 14.0 | 0 | 0 |

*Increase in antibody titre above the pre-immunised level assayed by radioimmunoassay (Smith R. and Lehner T., Clin. exp. Immunol. 43 417–428) and given in cpm.

EXAMPLE 3

Preparation of antigen X by enzyme digestion

This Example describes the production of antigen X using a bacterial protease. The starting material for these protease digestions was the 185,000 dalton molecular weight antigen which was eluted in the void volume of the Sephacryl 200 gel filtration column run in 4% SDS, as described in Example 1 d(ii). SDS gradient polyacrylamide gel electrophoresis (PAGE) of this starting material failed to detect any bands with a molecular weight lower than approximately 3500. The protease used was Staphylococcus Aureus V8 protease (Miles Laboratories Ltd.) at a weight:weight ratio of 1:20 of enzyme:185,000 daltons antigen I/II.

The starting antigen was dissolved in 50 mM NH$_4$HCO$_3$, pH 7.8, at a concentration of 2 mg/ml and boiled for 4 minutes. After cooling the solution to 37° C., the appropriate amount of protease, dissolved in the same buffer was added. The mixture was shaken and kept at 37° C. for the duration of the digestion. Digestion was continued for up to 17 hours at which time the enzyme was inactivated by boiling the solution. The resulting digested antigen was assayed by the solid phase radioimmunoassay for antigen activity and the molecular weight of the digestion products were investigated using SDS gradient PAGE and immuno-blotting. The major bands were at 4, 8, 10 and 12 k daltons and the 4 k daltons material was then separated by elution from SDS-polyacrylamide gels. One mg of protease-digested antigen was loaded onto an SDS-gradient polyacrylamide gel and electrophoresed. The gel was then sliced according to the prestained molecular weight markers (Bethesda Research Laboratories Inc. USA), and each slice was extracted for 24 hours at 37° C. with 0.01M Tris-HCl buffer (pH 8), containing 0.05% w/v SDS and 1 mM sodium azide. The extracts were dialysed extensively against methanol and water, lyophilised and reconstituted in 0.85% w/v NaCl. In this way a fraction of molecular weight 3800–4500 was isolated.

We claim:

1. Antigen X having the following characteristics:
   1. It has a molecular weight as determined by SDS-PAGE in the range of 3,800–4,500 daltons,
   2. It is immunogenic in experimental animals, forming precipitating antibodies,
   3. It reacts with antisera raised against antigen I, antigen I/II or antigen II as well as with antisera raised against itself, but does not react with antisera raised against antigen III,
   4. It is distinct from serotype polysaccharide antigens, glycerol teichoic acid, dextran and similar glucans, and does not synthesise glucans from sucrose,
   5. It is substantially of a proteinaceous nature,
   6. It absorbs ultra-violet light strongly between 220 and 250 nm (maximum at 230 nm),
   7. Its immunogenic activity is destroyed by the enzyme pronase.
   8. It is substantially free from antigen I/II.
   9. It induces production of helper T cells but not of suppressor T cells.

2. Antigen X according to claim 1 substantially free from antigenic materials having a molecular weight, determined by SDS-PAGE, less than 3800 daltons or greater than 4500 daltons.

3. Antigen X according to claim 1 obtained from the culture supernatant of Streptococcus mutans.

4. An anti-caries preparation comprising antigen X according to claim 1 together with a solid or liquid carrier.

5. A preparation according to claim 4 in a form suitable for parenteral or topical administration.

6. An antibody against antigen I/II that has been raised in a host that has been injected with antigen X according to claim 1.

7. A monoclonal antibody according to claim 6.

8. An anti-caries preparation comprising an antibody according to claim 6 together with a solid or liquid carrier.

9. A process for the production of antigen X as defined in claim 1 comprising subjecting antigen I/II obtained form culture supernatant of Streptococcus mutans in an excess quantity to polyacrylamide gel electrophoresis using a urea containing gel, and isolating from the gel fraction having a molecular weight in the range 3800–4500 daltons.

10. A process for the production of antigen X as defined in claim 1 comprising heating antigen I/II obtained from culture supernatant of Streptococcus mutans, subjecting the heated material to gel filtration and isolating from the gel a fraction having a molecular weight in the range 3800–4500 daltons.

11. A process according to claim 8 or 9 wherein the 3800–4500 daltons molecular weight fraction is subjected to polyacrylamide gel electrophoresis using a gel containing 15% w/w polyacrylamide and also containing urea and isolating a fraction of molecular weight 3800 daltons.

12. A process for the production of antigen X as defined in claim 1 comprising subjecting antigen I/II obtained from culture supernatant of *Streptococcus mutans* to treatment with a bacterial protease, subjecting the resulting material to polyacrylamide gel electrophoresis using a urea containing gel and isolating a fraction of molecular weight 3800–4500.

13. An anti-caries preparation comprising an antibody according to claim 7 together with a solid or liquid carrier.

14. A method for the treatment of a human or animal host to protect the host against dental caries which comprises administering to the host a preparation according to any one of claims 4, 5, 8 or 13.

* * * * *